United States Patent [19]

Kato

[11] Patent Number: 5,758,310

[45] Date of Patent: May 26, 1998

[54] APPARATUS FOR DETERMINING THE CONDITION OF AN AIR-FUEL RATIO SENSOR

[75] Inventor: Yoshihiko Kato, Susono, Japan

[73] Assignee: Toyota Jidosha Kabushiki Kaisha, Aichi, Japan

[21] Appl. No.: 763,882

[22] Filed: Dec. 11, 1996

[30] Foreign Application Priority Data

Dec. 20, 1995 [JP] Japan .................................... 7-331882

[51] Int. Cl.$^6$ ........................... F02D 41/14; G01M 15/00
[52] U.S. Cl. .................. 701/109; 73/23.32; 73/118.1; 123/688
[58] Field of Search ........................... 701/103, 104, 701/109; 73/23.31, 23.32, 118.1, 116, 117.3, 117.2; 123/688

[56] References Cited

U.S. PATENT DOCUMENTS

| | | | |
|---|---|---|---|
| 4,759,328 | 7/1988 | Blumel et al. | 123/688 |
| 5,036,820 | 8/1991 | Fujimoto et al. | 123/688 |
| 5,172,677 | 12/1992 | Suzuki | 123/688 |
| 5,392,643 | 2/1995 | O'Kennedy et al. | 73/118.1 |
| 5,454,259 | 10/1995 | Ishii et al. | 73/118.1 |
| 5,505,183 | 4/1996 | Sinha et al. | 73/118.1 |

FOREIGN PATENT DOCUMENTS

| | | |
|---|---|---|
| A-57-192852 | 11/1982 | Japan . |
| A-58-178248 | 10/1983 | Japan . |
| A-5-240829 | 9/1993 | Japan . |

*Primary Examiner*—George M. Dombroske
*Attorney, Agent, or Firm*—Oliff & Berridge, PLC

[57] ABSTRACT

An apparatus for determining whether or not an air-fuel ratio sensor, which is arranged in an exhaust system of an internal combustion engine to detect the air-fuel ratio of exhaust gas, is activated. The apparatus has a heater for heating the air-fuel ratio sensor, a detector for detecting whether or not the air-fuel ratio sensor has reached a half-activated state to start changing the output thereof after the start of the engine, a unit for integrating power supplied to the heater from the start of the engine until the air-fuel ratio sensor reaches the half-activated state, a unit for estimating, according to the integrated power, the power to be supplied to the heater to bring the air-fuel ratio sensor to a full-activated state, and a unit for determining that the air-fuel ratio sensor is in the full-activated state once the estimated power has completely been supplied to the heater.

4 Claims, 5 Drawing Sheets

APPARATUS FOR DETERMINING THE CONDITION OF AN AIR-FUEL RATIO SENSOR

BACKGROUND OF THE INVENTION

1. Field of the Invention

The present invention relates to an apparatus for determining the condition of an air-fuel ratio sensor and, more particularly, an apparatus for determining whether or not the air-fuel ratio sensor, which detects the air-fuel ratio of exhaust gas by detecting a limiting current which flows through a sensor element made of a solid electrolyte when voltage is impressed thereon, is activated.

2. Description of the Related Art

An air-fuel ratio sensor for detecting the air-fuel ratio of exhaust gas by detecting a limiting current which flows through a sensor element made of solid electrolyte when voltage is impressed there on and convert the limiting current to signal voltage, is known in the above described type of air-fuel ratio sensor, the limiting current varies in accordance with a change in the sensor element temperature as shown in FIG. 3.

As shown in FIG. 3, no limiting current flows until the sensor element temperature increases to some value. Then the limiting current begins to flow. The current increases in accordance with an increase in temperature, i.e. the sensitivity to a change in the air-fuel ratio increases in accordance with an increase in the temperature, and finally the current is stabilized when the temperature becomes higher than some value.

Namely, the air-fuel ratio sensor correctly detects an air-fuel ratio only after it is heated up to the activation temperature.

To quickly activate the sensor, it is known to provide the air-fuel ratio sensor with an electric heater.

The heater will be broken if excessive electric power is supplied thereto. If the supplied electric power is too small, the output voltage of the sensor will drop to deteriorate detecting accuracy. It is necessary, therefore, to supply proper electric power to the heater. For this purpose, it is necessary to determine whether or not the sensor is in a full-activated state.

To determine whether or not the air-fuel ratio sensor is activated, Japanese Unexamined Patent Publication Nos. 57-192852 and 58-178248 apply an alternating voltage to the sensor and measure the internal resistance of the sensor. Another prior art applies a negative voltage to the sensor, monitors the output of the sensor, and determines whether or not the sensor is activated.

These prior arts involve high cost because they need a circuit for switching the voltages to apply.

The prior art that alternately measures a limiting current and resistance cannot detect an air-fuel ratio while it is measuring resistance. Accordingly, while the sensor is in the half-activated state, this prior art is unable to apply feedback-control according to the rich/lean state of the air-fuel ratio, although it is possible to determine the rich/lean state in the half-activated state.

An object of the present invention is to provide an apparatus capable of correctly determining whether or not an air-fuel ratio sensor is activated at low cost without interrupting the use of signals.

SUMMARY OF THE INVENTION

Therefore, an object of the present invention is to provide an apparatus which can determine the state of an air-fuel ratio sensor at low cost and with high accuracy.

According to the present invention there is provided an apparatus for determining whether or not an air-fuel ratio sensor, which is arranged in an exhaust system of an internal combustion engine to detect the air-fuel ratio of exhaust gas, is activated. The apparatus has a heater for heating the air-fuel ratio sensor, a detector for detecting whether or not the air-fuel ratio sensor has reached a half-activated state to start changing the output thereof after the start of the engine, a unit for integrating power supplied to the heater from the start of the engine until the air-fuel ratio sensor reaches the half-activated state, a unit for estimating, according to the integrated power, the power to be supplied to the heater to bring the air-fuel ratio sensor to a full-activated state, and a unit for determining that the air-fuel ratio sensor is in the full-activated state once the estimated electric power has completely been supplied to the heater.

The present invention will be more fully understood from the description of the preferred embodiments of the invention set forth below, together with the accompanying drawings.

DESCRIPTION OF THE PREFERRED EMBODIMENTS

Figure 1:
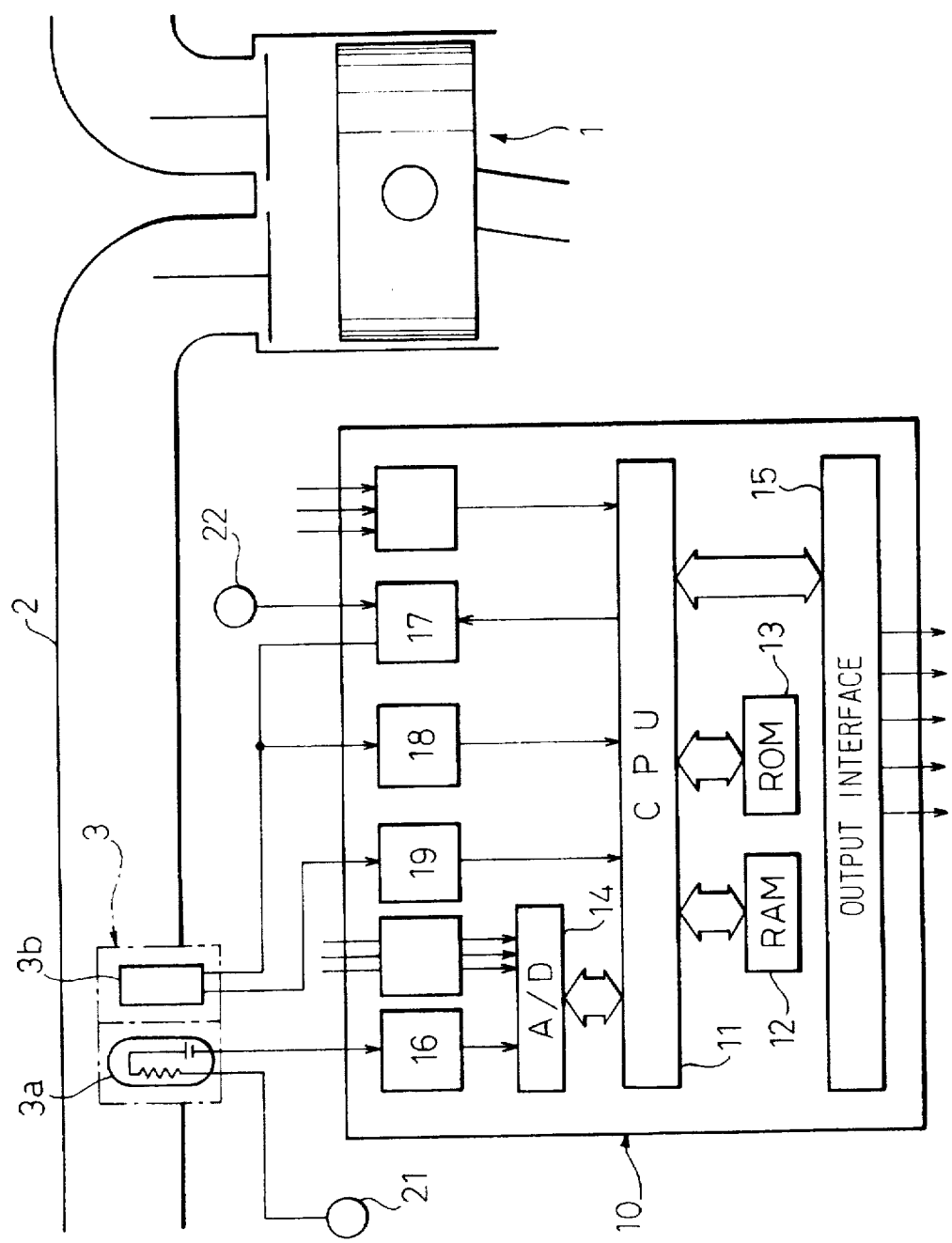
FIG. 1 schematically shows a construction of an embodiment of the present invention.

FIG. 1 schematically shows a construction of an embodiment of the present invention. An engine 1 has an exhaust pipe 2 provided with an air-fuel ratio sensor 3. The sensor 3 consists of a sensor element 3a made of a solid electrolyte and a heater 3b for heating the element 3a.

An engine control computer (ECU) 10 is a digital computer having a CPU (microprocessor) 11, a RAM (random access memory) 12, a ROM (read only memory) 13, an AD converter 14, and an output interface 15. These parts are connected to one another. The ECU 10 has additional parts mentioned below according to the present invention.

A drive circuit 16 has a resistor for detecting a current passing through the element 3a to which a power source 21 applies a voltage. The driver circuit 16 also has an amplifier for amplifying a voltage drop in the resistor according to a given amplification factor. The drive circuit 16 supplies an output voltage to the CPU 11 through the AD converter 14.

A heater controller circuit 17 controls power supplied from a heater power source 22 to the heater 3b in response to a control signal from the CPU 11.

A heater voltage detector circuit 18 detects a voltage applied to the heater 3b after the heater is energized. A heater current detector circuit 19 detects a current passing through the heater 3b after the heater is energized.

The CPU 11 carries out operations mentioned below according to signals from the above-mentioned parts and determines whether or not the element 3a of the air-fuel ratio sensor 3 is active.

The CPU 11 also receives signals from other sensors through an input interface and the AD converter 14 and supplies control signals through the output interface 15, to control, for example, fuel injection and ignition timing.

The principle of the present invention will be explained.

Figure 2:
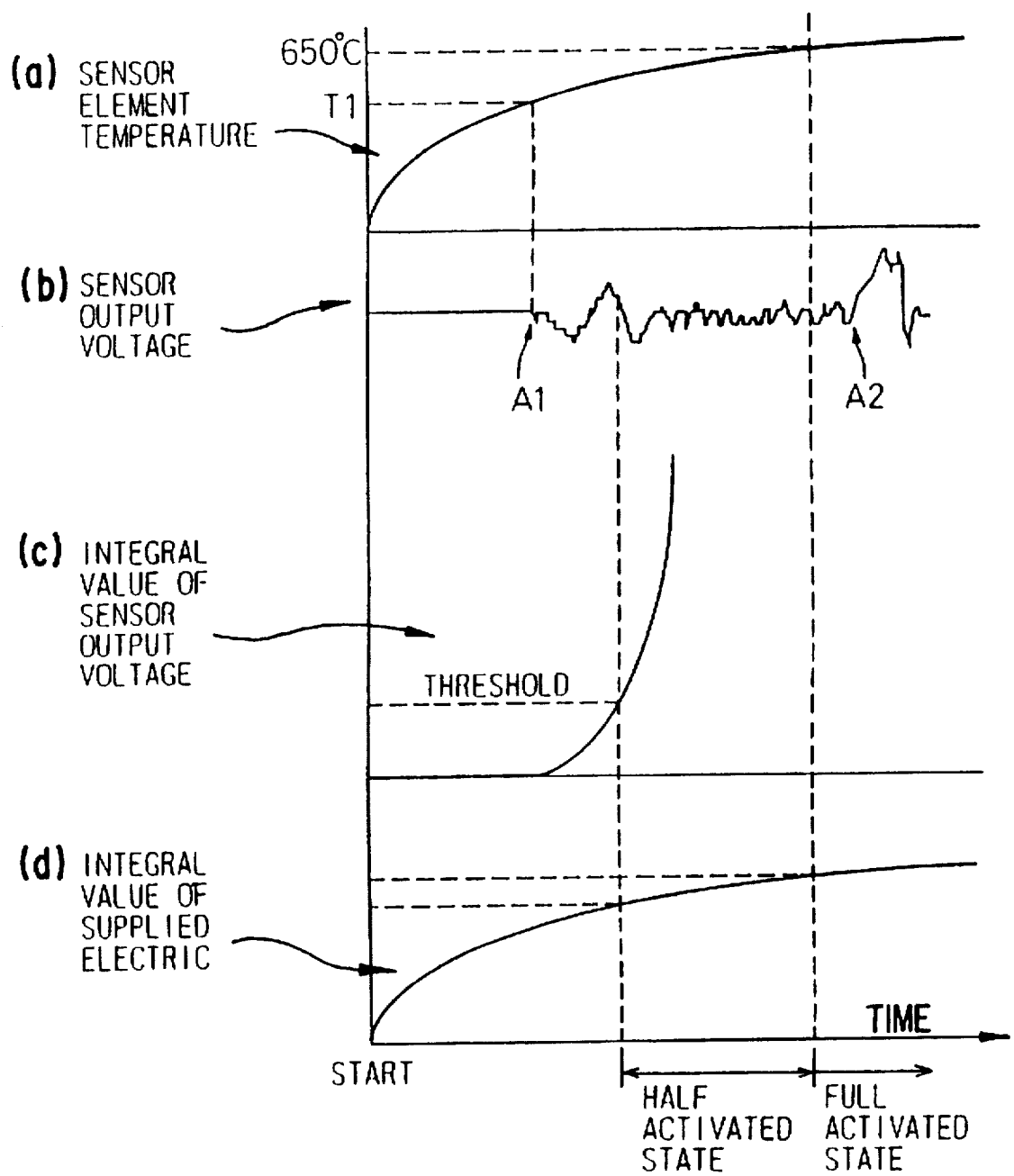
FIG. 2(a)–(d) is a time chart showing the principle of the present invention.

FIG. 2 is a time chart showing the principle of the present invention. Chart (a) of FIG. 2 shows changes in the temperature of the element 3a of the air-fuel ratio sensor 3 after the engine is started. Chart (b) of FIG. 2 shows changes in the output voltage of the sensor 3.

For a while after the start of the engine, no limiting current flows because the temperature of the element 3a is low. Accordingly, the output voltage of the sensor 3 corresponds to a stoichiometric air-fuel ratio. The reason of this will be explained.

The sensor 3 and drive circuit 16 of the embodiment are the same as those of Japanese Unexamined Patent Publication No. 5-240829. The potential of the element 3a on the exhaust gas side is set to be higher than the ground level of the drive circuit 16. An output voltage Eo of the sensor 3 is expressed as follows:

$$Eo=Vo+Vr+IR \quad (1)$$

where Vo is a potential, Vr is an applied voltage, I is a limiting current passing through the element 3a, and R is resistance for converting the limiting current into a voltage.

When the temperature of the element 3a is low, there is no limiting current I, and therefore, Eo=Vo+Vr The formula (1) is written as follows:

$$Eo=Vo+Vr+K(\lambda-1)R \quad (2)$$

where K is a proportional constant and $\lambda$ is an excess air ratio.

If $\lambda=1$, i.e., if it is a theoretical air-fuel ratio, $\lambda-1=0$, and therefore, Eo=Vo+Vr.

Namely, if there is no limiting current due to a low temperature of the element 3a, the output voltage Eo is equal to that with a stoichiometric air-fuel ratio.

When the element 3a reaches a temperature T1, the output voltage of the sensor 3 starts to change at a point A1.

The output voltage of the sensor 3 after the start of the engine is integrated as shown in chart (c) of FIG. 2. When the integral exceeds a given threshold, the element 3a becomes half-activated, and a point of the exceeding the threshold is named the half-activated point.

At the same time, power supplied to the heater 3b is integrated as shown in chart (d) of FIG. 2.

Figure 3:
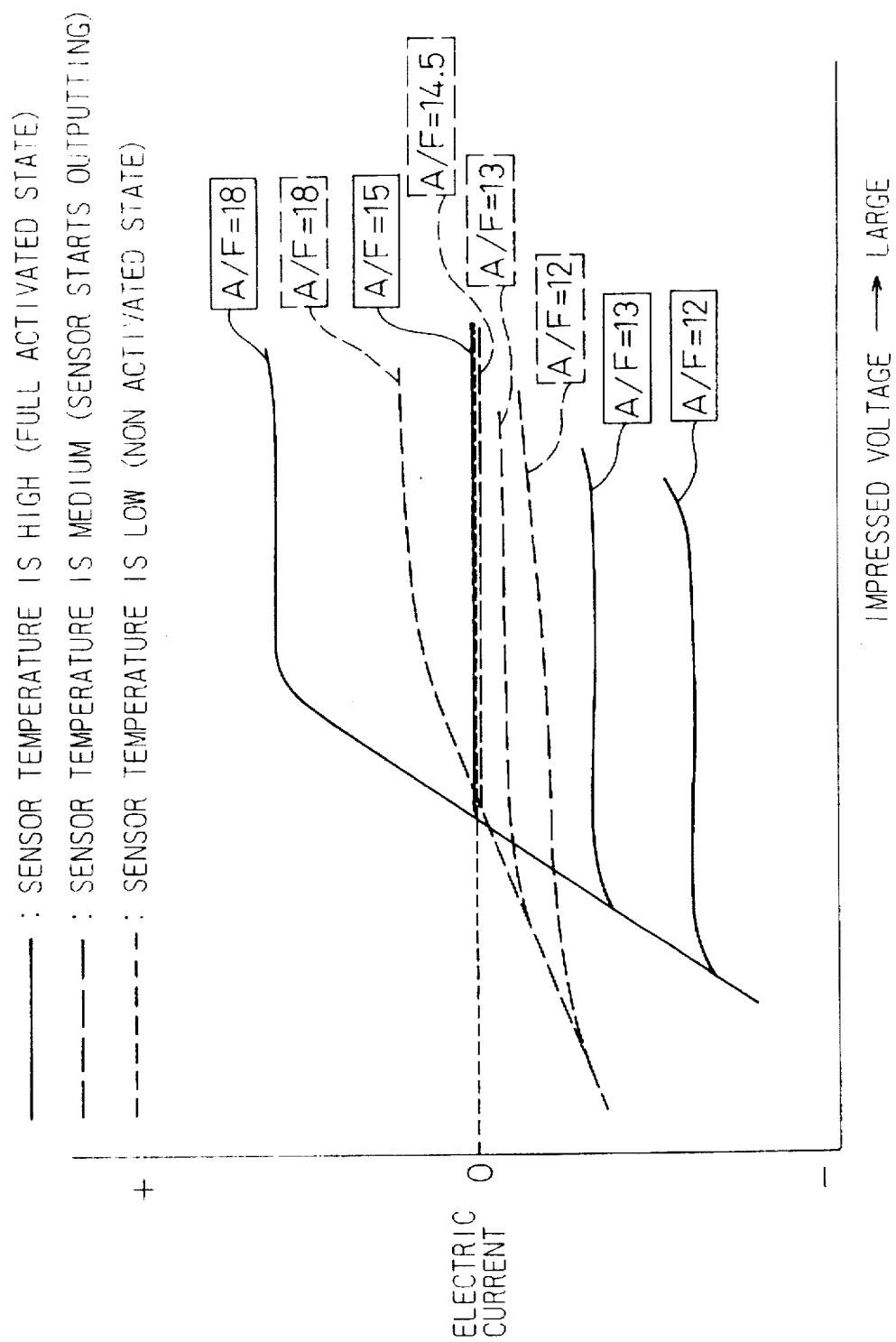
FIG. 3 shows changes in a limiting current flowing through an air-fuel ratio sensor.

The element 3a is further heated to reach a full-activated state. Then, the limiting current flowing through the element 3a greatly changes in response to an air-fuel ratio as indicated with continuous lines in FIG. 3. Namely, the output voltage of the sensor 3 starts to greatly change from a point A2 where the full-activated state starts.

The temperature at which the element 3a enters the half-activated state is about 550° C. in this embodiment, and the temperature at which the element 3a enters the full-activated state is about 650° C. in this embodiment. This means that the element 3a in the half-activated state will reach the full-activated state if a given amount of power is supplied to the heater 3b. Namely, if the half-activated state is determinable, the full-activated state is also determinable.

If the engine is started at a high temperature, the element 3a is hot because the temperature ambient air around the sensor 3 is high. If the temperature of the element 3a having a full-activation temperature of 650° C. is, for example, 600° C. when the engine is started, the element 3a quickly reaches the half-activated state and full-activated state because of a high ambient air temperature. If a fixed amount of electric power is supplied to the heater 3b under this situation, the element 3a will overheat and the heater 3b will break.

Figure 4:
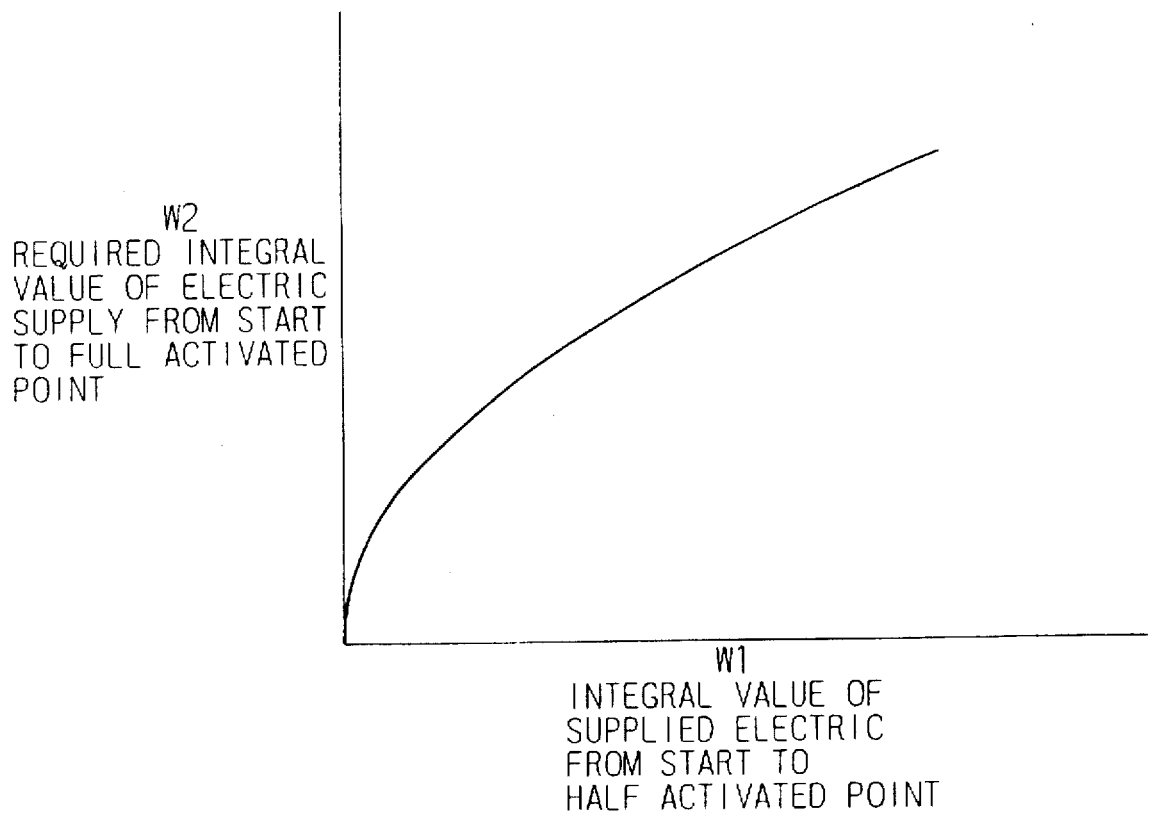
FIG. 4 shows a relationship between cumulative electric power up to a half-activated state and cumulative power up to a full-activated state of the air-fuel ratio sensor.

Accordingly, the present invention finds a relationship between cumulative electric power W1 necessary for bringing the element 3a to the half-activated state and cumulative power W2 necessary for bringing the element 3a to the full-activated state as shown in FIG. 4. The relationship is stored as a map in the ROM 13. Then, cumulative electric power for bringing the element 3a to the full-activated state is obtained according to cumulative electric power supplied to bring the element 3a to the half-activated state, as shown in chart (d) of FIG. 2.

Once it is detected that the cumulative power for bringing the element 3a to the full-activated state has completely been supplied to the heater 3b, it is determined that the element 3a is in the full-activated state.

Figure 5:
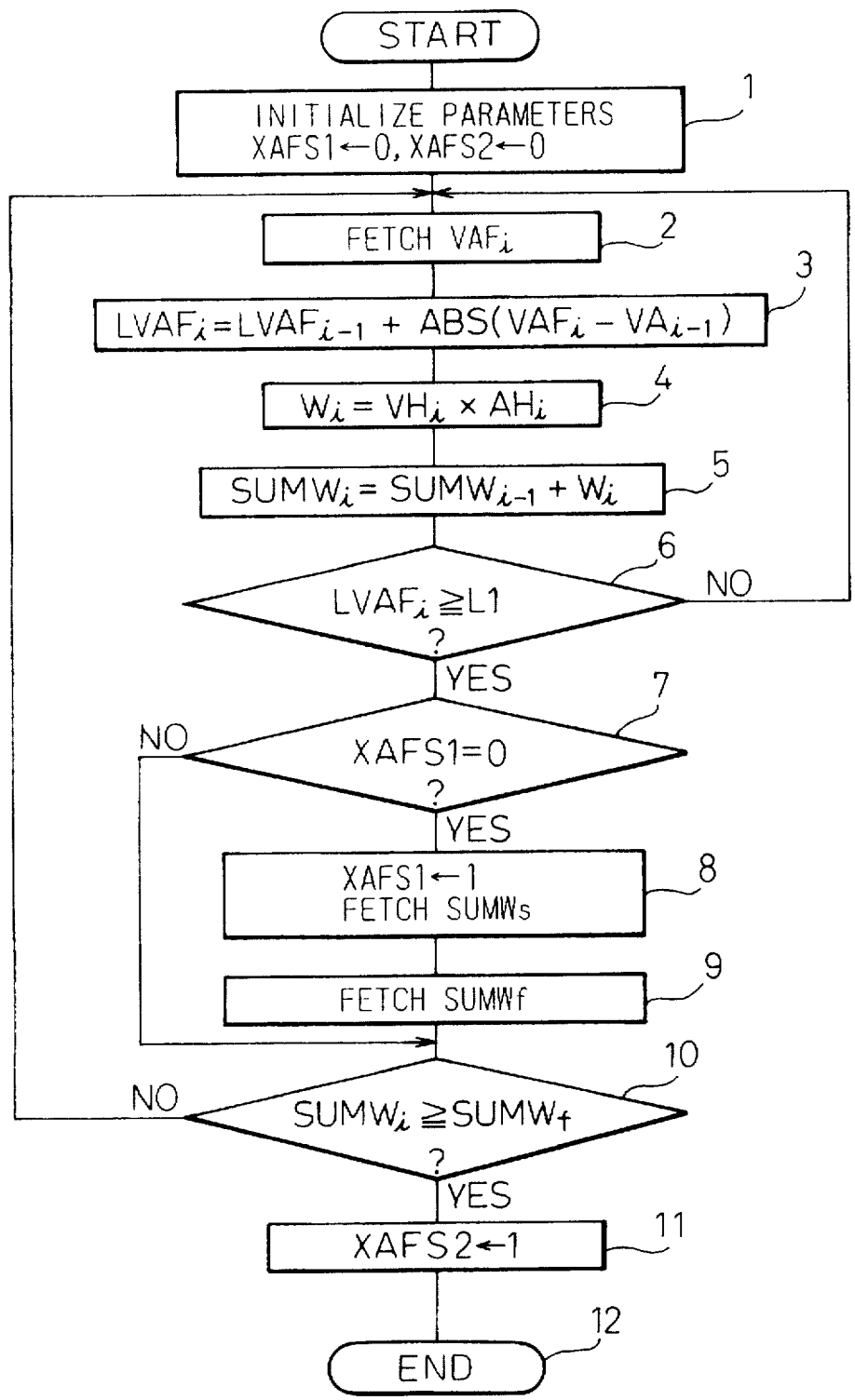
FIG. 5 is a flowchart showing an operation of the embodiment.

FIG. 5 is a flowchart showing a routine of determining whether or not the element 3a of the air-fuel ratio sensor 3 is in the full-activated state according to the present invention.

The routine is started when the engine is started and is terminated when the element 3a reaches the full-activated state.

Step 1 initializes engine controlling parameters stored in the RAM 12, a flag XAFS1 for indicating that the element 3a is in the half-activated state, and a flag XAFS2 for indicating that the element 3a is in the full-activated state. Step 2 reads an output VAF of the air-fuel ratio sensor 3.

Step 3 calculates an integral LVAF of the output VAF as follows:

$$LVAFi=LVAFi-1+ABS(VAFi-VAFi-1)$$

where VAFi-1 is a preceding output of the sensor 3, VAFi is the present output thereof, and ABS(VAFi-VAFi-1) is an absolute difference between the present output VAFi and the preceding output VAFi-1.

Step 4 calculates power Wi supplied to the heater 3b according to the product of a voltage VHi detected by the heater voltage detector 18 and a current AHi detected by the heater current detector 19. Step 5 calculates cumulative electric power SUMWi from the start of supply of power.

Step 6 determines whether or not the integral LVAFi is greater than a threshold L1. If LVAFi≧L1, it is determined that the element 3a is in the half-activated state, and step 7 checks to see if XAFS1=0. If the flag XAFS1 is 0, step 8 sets the flag XAFS1 to 1 and substitutes the cumulative electric power SUMWi for SUMWs. If LVAFi<L1 in step 6, the flow returns to step 2 until LVAF exceeds L1.

Step 9 searches, according to SUMWs, the map stored in the ROM 13 for cumulative power SUMWf to bring the element 3a to the full-activated state. Step 10 checks to see if SUMWi≧SUMWf. If SUMWi≧SUMWf, step 11 sets the flag XAF2 to 1 to indicate that the element 3a is in the full-activated state. Step 12 terminates the routine. If SUMWi<SUMWf in step 10, the flow returns to step 2 until SUMWi exceeds SUMWf.

In this embodiment, the cumulative power SUMWf used to see whether or not the element 3a is in the full-activated state is an accumulation of electric power supplied to the heater 3b after the activation thereof until the element 3a is put in the full-activated state. The cumulative power SUMWf may be an accumulation of electric power supplied to the heater 3b after the element 3a is put in the half-activated state until the same reaches the full-activated state.

In this case, a corresponding actual electric power supplied must be counted after the half-activated state. Namely, cumulative electric power must be cleared as soon as the flag XAFS1 is set to 1 and must again be integrated.

As explained above, the present invention determines whether or not the air-fuel ratio sensor is in the half-activated state in which the sensor output starts changing, and calculates cumulative electric power for bringing the sensor to the full-activated state according to cumulative electric power consumed to bring the sensor to the half-activated state. The cumulative electric power for bringing the sensor to the full-activated state reflects the temperature of the sensor at the start of the engine. Consequently, the present invention correctly determines whether or not the sensor is in the half- or full-activated state.

The present invention determines whether or not the sensor is in the half- or full-activated state without an alternating voltage or a negative voltage. Namely, the present invention allows the output voltage of the sensor to be used anytime. Even during an intermediate period between the half-activated state and the full-activated state, the output voltage of the sensor is usable to determine whether an air-fuel ratio is rich or lean to allow feedback-control of fuel injection.

I claim:

1. An apparatus for determining whether or not an air-fuel ratio sensor, which is arranged in an exhaust system of an internal combustion engine to detect the air-fuel ratio of exhaust gas, is activated, comprising:

a heater for heating the air-fuel ratio sensor;

means for detecting whether or not the air-fuel ratio sensor has reached a half-activated state to start changing the output thereof after the start of the engine;

means for integrating power supplied to the heater from the start of the engine until the air-fuel ratio sensor reaches the half-activated state;

means for estimating, according to the integrated power, power to be supplied to the heater to bring the air-fuel ratio sensor to a full-activated state; and means for determining that the air-fuel ratio sensor is in the full-activated state once the estimated power has completely been supplied to the heater.

2. An apparatus according to claim 1, wherein said air-fuel ratio sensor detects the air-fuel ratio of exhaust gas by detecting a limiting current which flows through a sensor element made of a solid electrolyte when a voltage is impressed thereon.

3. An apparatus according to claim 2, wherein a potential of said sensor element on the exhaust gas side is set to be higher than the ground level of a circuit for detecting a limiting passing through said sensor element.

4. An apparatus according to claim 1, wherein said means for detecting the half-activated state determines that said air-fuel ratio sensor is in the half-activated state when the length of an output signal response curve of said air-fuel ratio sensor exceeds a predetermined threshold.

* * * * *